(12) United States Patent
Eddy

(10) Patent No.: US 9,877,875 B2
(45) Date of Patent: *Jan. 30, 2018

(54) ANTIMICROBIAL HYDROGEL FORMULATION

(71) Applicant: Patrick E Eddy, Allendale, MI (US)

(72) Inventor: Patrick E Eddy, Allendale, MI (US)

(73) Assignee: Parasol Medical LLC, Buffalo Grove, IL (US)

( * ) Notice: Subject to any disclaimer, the term of this patent is extended or adjusted under 35 U.S.C. 154(b) by 164 days.

This patent is subject to a terminal disclaimer.

(21) Appl. No.: 14/049,319

(22) Filed: Oct. 9, 2013

(65) Prior Publication Data

US 2014/0100504 A1    Apr. 10, 2014

Related U.S. Application Data

(60) Provisional application No. 61/711,421, filed on Oct. 9, 2012.

(51) Int. Cl.
*A61F 13/02*    (2006.01)
*A61F 13/00*    (2006.01)
(Continued)

(52) U.S. Cl.
CPC .... *A61F 13/0253* (2013.01); *A61F 13/00063* (2013.01); *A61L 15/26* (2013.01);
(Continued)

(58) Field of Classification Search
CPC .................................................. A61F 13/0253
See application file for complete search history.

(56) References Cited

U.S. PATENT DOCUMENTS 4,865,844 A * 9/1989 Blank ............... A61K 31/695
424/404
5,079,004 A    1/1992 Blank et al.
(Continued)

FOREIGN PATENT DOCUMENTS

WO    2008097599 A2    8/2008

OTHER PUBLICATIONS

Murray et al., "Microbial Inhibition on Hospital Garments Treated with Dow Corning 5700 Antimicrobial Agent," Journal of Clinical Microbiology, vol. 26, No. 9, Sep. 1988, pp. 1884-1886.

*Primary Examiner* — Tarla Patel
(74) *Attorney, Agent, or Firm* — Price Heneveld LLP

(57) ABSTRACT

A hydrogel formulation is provided for use with a film. The hydrogel formulation includes a medical-grade hydrogel and an antimicrobial substance. This hydrogel formulation may be coated onto one or more surfaces of a medical-grade transparent film suitable for a wound dressing. The antimicrobial material may be a silane quaternary ammonium salt. The silane quaternary ammonium salt may comprise 3-(trimethoxysilyl) propyldimethyloctadecyl ammonium chloride. The 3-(trimethoxysilyl) propyldimethyloctadecyl ammonium chloride may constitute about 72% by weight of the silane quaternary ammonium salt. The medical-grade hydrogel may comprise a colloidal gel in which the particles are dispersed in water. Further, the hydrogel formulation may include about 0.01% to about 60% by weight of the antimicrobial substance. The transparent film may further include a release liner applied over the coated side(s) of the transparent film. The transparent film may comprise polyurethane.

13 Claims, 2 Drawing Sheets

(51) Int. Cl.
*A61L 15/26* (2006.01)
*A61L 15/46* (2006.01)
*A61L 15/58* (2006.01)

(52) U.S. Cl.
CPC ............... *A61L 15/46* (2013.01); *A61L 15/58* (2013.01); *A61L 2300/208* (2013.01); *A61L 2300/404* (2013.01)

(56) References Cited

U.S. PATENT DOCUMENTS

| | | | |
|---|---|---|---|
| 5,183,664 A * | 2/1993 | Ansell | A61F 13/023 128/849 |
| 5,270,358 A * | 12/1993 | Asmus | A61L 24/043 424/448 |
| 5,428,078 A | 6/1995 | Cohen et al. | |
| 5,959,014 A | 9/1999 | Liebeskind et al. | |
| 6,224,579 B1 | 5/2001 | Modak et al. | |
| 6,495,229 B1 | 12/2002 | Carte et al. | |
| 6,821,943 B2 | 11/2004 | Avery et al. | |
| 7,045,673 B1 | 5/2006 | Batich et al. | |
| 7,709,694 B2 | 5/2010 | Batich et al. | |
| 7,790,217 B2 | 9/2010 | Toreki et al. | |
| 8,025,120 B2 | 9/2011 | Eddy | |
| 8,491,922 B2 | 7/2013 | Eddy | |
| 2007/0042198 A1 * | 2/2007 | Schonemyr | A01N 25/34 428/447 |
| 2007/0218096 A1 | 9/2007 | Wooley | |
| 2008/0260804 A1 | 10/2008 | Morris et al. | |
| 2009/0215917 A1 | 8/2009 | Trotter et al. | |
| 2009/0285890 A1 * | 11/2009 | Van Den Plas | A01N 31/16 424/484 |
| 2009/0312684 A1 * | 12/2009 | Leonard | A01N 25/10 602/44 |
| 2012/0173274 A1 | 7/2012 | Rensvold et al. | |

* cited by examiner

ANTIMICROBIAL HYDROGEL FORMULATION

CROSS-REFERENCE TO RELATED APPLICATION

This application claims priority under 35 U.S.C. § 119(e) upon U.S. Provisional Patent Application No. 61/711,421, entitled "ANTIMICROBIAL HYDROGEL FORMULATION" filed on Oct. 9, 2012, by Patrick E. Eddy, the entire disclosure of which is incorporated herein by reference.

BACKGROUND OF THE INVENTION

The embodiments described herein generally relate to a hydrogel formulation and to medical supplies including hydrogel formulations such as film dressings, and more particularly IV securement dressings, and wound dressings.

SUMMARY OF THE INVENTION

According to an embodiment of the present invention, a transparent film dressing is provided that comprises a transparent film and a hydrogel adhesive formulation coated on one or more sides of the transparent film. The transparent film comprises polyurethane. The hydrogel formulation comprises a medical-grade hydrogel and an antimicrobial substance, wherein the medical-grade hydrogel comprises a colloidal gel in which the particles are dispersed in water. The antimicrobial material is a silane quaternary ammonium salt comprising 3-(trimethoxysilyl) propyldimethyloctadecyl ammonium chloride. The 3-(trimethoxysilyl) propyldimethyloctadecyl ammonium chloride may constitute about 72% by weight of the silane quaternary ammonium salt. The hydrogel formulation may include about 0.01% to about 60% by weight of the antimicrobial substance. The transparent film dressing may further comprise a release liner applied over one or more coated sides of the transparent film.

According to another embodiment of the present invention, a hydrogel formulation is provided for use on a film dressing, the hydrogel formulation comprising a medical-grade hydrogel and an antimicrobial substance. The film dressing may be transparent or opaque.

According to another embodiment of the present invention, a transparent film dressing is provided that comprises a transparent film having a hydrogel adhesive formulation coated on one or more sides, where the hydrogel formulation comprises a medical-grade hydrogel and an antimicrobial substance. The transparent film dressing may further include a release liner applied over the coated side(s) of the transparent film. The transparent film may comprise polyurethane.

In the latter two embodiments, the antimicrobial material may be a silane quaternary ammonium salt. The silane quaternary ammonium salt may comprise 3-(trimethoxysilyl) propyldimethyloctadecyl ammonium chloride. The 3-(trimethoxysilyl) propyldimethyloctadecyl ammonium chloride may constitute about 72% by weight of the silane quaternary ammonium salt.

Also in these two embodiments, the medical-grade hydrogel may comprise a colloidal gel in which the particles are dispersed in water. Further, the hydrogel formulation may include about 0.01% to about 60% by weight of the antimicrobial substance.

These and other features, advantages, and objects of the present invention will be further understood and appreciated by those skilled in the art by reference to the following specification, claims, and drawings.

DETAILED DESCRIPTION OF PREFERRED EMBODIMENTS

Reference will now be made in detail to the present preferred embodiments of the invention.

A novel hydrogel formulation for film dressings is disclosed herein that not only provides the requisite properties for a hydrogel, but also eliminates bacteria on contact. In general, the hydrogel formulation comprises a hydrogel and an antimicrobial substance, such as a silane quaternary ammonium salt. The hydrogel may be a medical-grade colloidal gel in which the particles are dispersed in water. Preferred commercially available silane quaternary ammonium salts include: MicrobeCare™ XLP, which is available from MicrobeCare, LLC of Allendale, Mich.; "PROMOFRESH X 105" from Piedmont Chemical Industries I, LLC of High Point, N.C.; and AEM 5772 Antimicrobial, which is available from Aegis Environments of Midland, Mich. These particular antimicrobial substances include an active ingredient of about 72% by weight 3-(trimethoxysilyl) propyldimethyloctadecyl ammonium chloride and about 28% by weight inert ingredients. The antimicrobial substance could also be AEGIS Microbe Shield™ (from Aegis Environments, Midland, Mich.), which is a copolymer of chloropropyltrihydroxysilane and octadecylaminodimethyltrihydroxysilylpropyl ammonium chloride.

Silane quaternary ammonium salts are particularly well suited for the antimicrobial material as they are long lasting and capable of emitting ions that aid in the destruction of a microbe. In addition, they are organofunctional silanes that include a monomer including a silane, a positively charged nitrogen molecule, and a long molecular chain. The silane bases of these monomers can covalently and permanently bond to each other and any surface. In addition, silane quaternary ammonium salts are preferable as they are substantially free from arsenic, silver, tin, heavy metals and polychlorinated phenols. Also, they are safe to apply to the skin or to a wound of a patient.

Microbes may include bacteria, mold, mildew, algae, etc. The cell membranes of the microbes are attracted to, and then are punctured by, the long molecular chains of the monomers. As the microbes are drawn closer because of the positive-negative ion exchanges, the monomers penetrate further into the cell membranes. Once the cell membranes are penetrated deeply, they are physically ruptured by a sword-like action and then electrocuted by positively charged nitrogen molecules of the monomers, thus destroying the microbes. Thus, the microbes are eliminated without "using up" any of the antimicrobial active ingredients, which remain in the adhesive formulation ready to continue protecting the patient against further microbial contamination.

The antimicrobial substance may be mixed into the hydrogel in various amounts of anywhere from about 0.01% to about 60% by weight to achieve the desired degree of antimicrobial activity while not compromising the desirable properties of the hydrogel in the resulting mixture.

Figure 1:
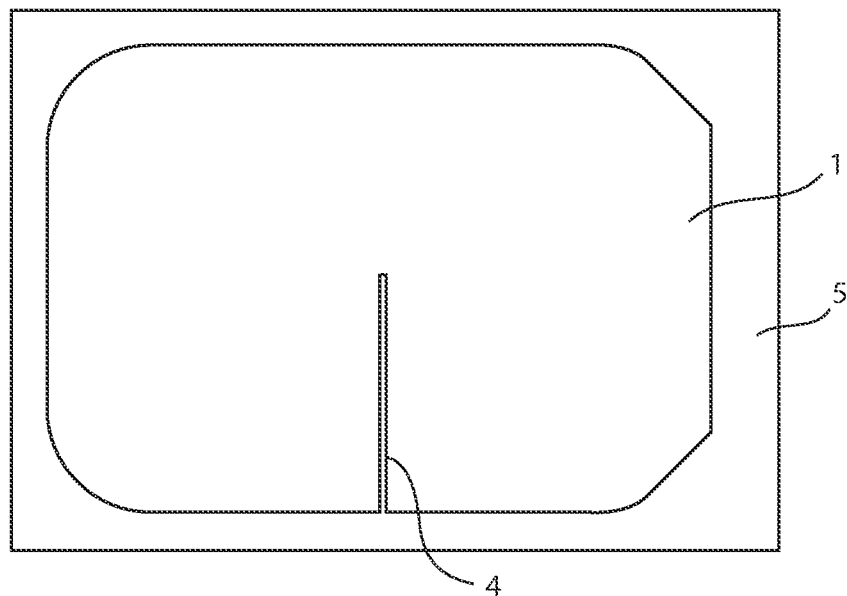
FIG. 1 is a front elevational view of an IV securement dressing according to a first embodiment.
Figure 2:
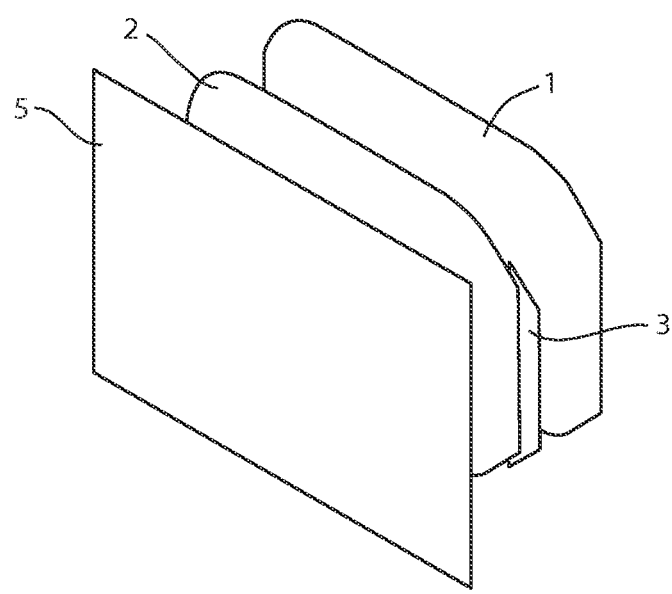
FIG. 2 is an exploded perspective view of the IV securement dressing shown in FIG. 1.
Figure 3:
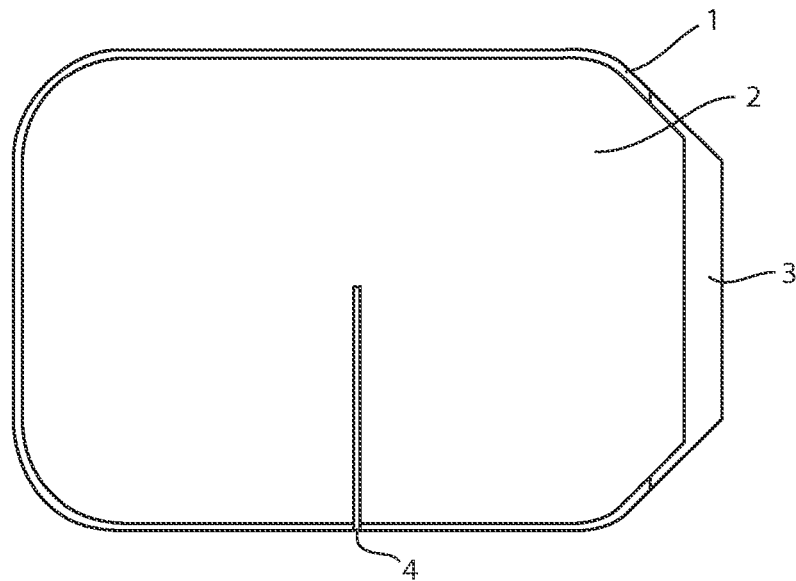
FIG. 3 is a front elevational view of an IV securement dressing according to a second embodiment.
Figure 4:
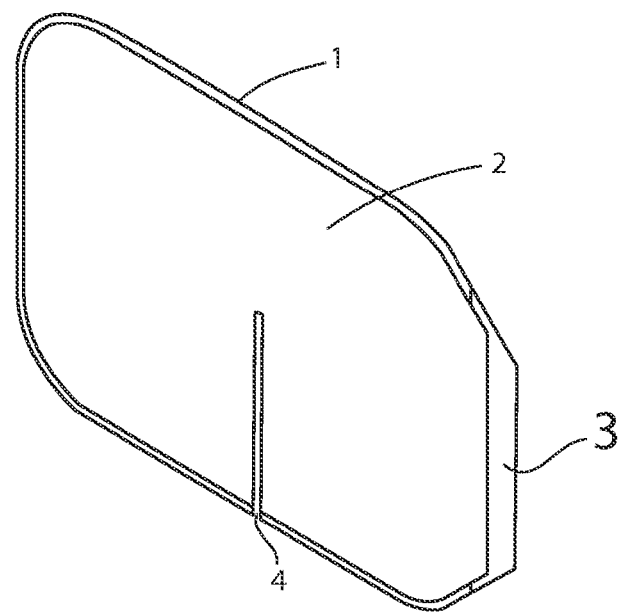
FIG. 4 is a perspective view of the IV securement dressing shown in FIG. 3.

As shown in the drawings, the hydrogel formulation 2 is coated on one side or both sides of a medical-grade film 1 (i.e., plastic carrier), which may be a transparent film of the type commonly used for wound dressings or securing an intravenous (IV) needle or catheter. One suitable transparent film is a 1-mil polyurethane film available from DermaMed Coatings Company, LLC of Tallmadge, Ohio. The film 1 is preferably oxygen permeable and may have an optional slit 4 for an IV needle or catheter. The coating method may be a knife-over-roll method. According to a first embodiment shown in FIGS. 1 and 2, a release liner 5 may be applied to the coated side(s) of the transparent film 1. A woven fabric piece 3 may be provided at one end of the film 1. In the second embodiment shown in FIGS. 3 and 4, a release liner 5 is not used.

The hydrogel-coated transparent film may be used as a wound dressing or for any other medical use such as securing an IV needle to a patient or securing a catheter.

The film may also be opaque and may be of the type that is commonly used for bandages or medical tape.

Modifications of the invention will occur to those skilled in the art and to those who make or use the invention. Therefore, it is understood that the embodiments described above are merely for illustrative purposes and not intended to limit the scope of the invention, which will be defined by claims as interpreted according to the principles of patent law, including the doctrine of equivalents.

What is claimed is:

1. A transparent film dressing comprising:
   a transparent film, wherein said transparent film comprises polyurethane; and
   a hydrogel adhesive formulation coated on one or more sides of said transparent film,
   wherein said hydrogel adhesive formulation comprises a medical-grade hydrogel and an antimicrobial substance, wherein said medical-grade hydrogel comprises a colloidal gel in which particles are dispersed in water,
   wherein said antimicrobial substance is a silane quaternary ammonium salt comprising 3-(trimethoxysilyl) propyldimethyloctadecyl ammonium chloride.

2. The transparent film dressing of claim 1 and further comprising a release liner applied over one or more coated sides of said transparent film.

3. The transparent film dressing of claim 1, wherein said 3-(trimethoxysilyl) propyldimethyloctadecyl ammonium chloride constitutes about 72% by weight of the silane quaternary ammonium salt.

4. The transparent film dressing of claim 3, wherein said hydrogel adhesive formulation includes about 0.01% to about 60% by weight of said antimicrobial substance.

5. The transparent film dressing of claim 1, wherein said hydrogel adhesive formulation includes about 0.01% to about 60% by weight of said antimicrobial substance.

6. A transparent film dressing comprising:
   a transparent film; and
   a hydrogel adhesive formulation coated on one or more sides of said transparent film,
   wherein said hydrogel adhesive formulation comprises a medical-grade hydrogel and an antimicrobial substance, wherein said antimicrobial substance is a silane quaternary ammonium salt.

7. The transparent film dressing of claim 6 and further comprising a release liner applied over one or more coated sides of said transparent film.

8. The transparent film dressing of claim 6, wherein said transparent film comprises polyurethane.

9. The transparent film dressing of claim 6, wherein said silane quaternary ammonium salt comprises 3-(trimethoxysilyl) propyldimethyloctadecyl ammonium chloride.

10. The transparent film dressing of claim 9, wherein said 3-(trimethoxysilyl) propyldimethyloctadecyl ammonium chloride constitutes about 72% by weight of the silane quaternary ammonium salt.

11. The transparent film dressing of claim 10, wherein said medical-grade hydrogel comprises a colloidal gel in which particles are dispersed in water.

12. The transparent film dressing of claim 6, wherein said medical-grade hydrogel comprises a colloidal gel in which particles are dispersed in water.

13. The transparent film dressing of claim 6, wherein said hydrogel adhesive formulation includes about 0.01% to about 60% by weight of said antimicrobial substance.

* * * * *